United States Patent [19]
Baba et al.

[11] Patent Number: 5,442,077
[45] Date of Patent: Aug. 15, 1995

[54] BENZO[B]FURANCARBOXAMIDE DERIVATIVES, PROCESS FOR THE PREPARATION OF SAME AND USE THEREOF FOR IMPROVING HYPERMOTILITY

[75] Inventors: Yutaka Baba; Toshinao Usui; Noriyuki Iwata; Takuji Kakigami; Yoshiro Ozeki; Katsura Tsukamoto; Nobuyuki Ito, all of Aichi, Japan

[73] Assignee: Sanwa Kagaku Kenkyusho Co., Ltd., Aichi, Japan

[21] Appl. No.: 285,719

[22] Filed: Aug. 4, 1994

[30] Foreign Application Priority Data

Aug. 24, 1993 [JP] Japan ................... 5-209242
May 24, 1994 [JP] Japan ................... 6-109491

[51] Int. Cl.⁶ .................. C07D 487/04; A61K 31/40
[52] U.S. Cl. ..................... 548/453; 514/414
[58] Field of Search .................. 548/453; 514/414

[56] References Cited

FOREIGN PATENT DOCUMENTS 60-169473 12/1984 Japan .
62-129279 8/1986 Japan .
62-277376 1/1987 Japan .
62-234083 2/1987 Japan .
1-104072 7/1988 Japan .
1-110684 9/1988 Japan .
1-501226 4/1989 Japan .
1-168686 7/1989 Japan .
4-295476 12/1991 Japan .

OTHER PUBLICATIONS

*Naunyn–Schmiedeberg's Arch. Pharmacol.*, vol. 343, p. 439 (1991).
"Abstract of the 98th Annual Lecture Meeting in the Pharmacological Society of Japan", p. 223 (1978).
*Bulletin of Pharmacological Society of Japan*, vol. 92, p. 297 (1988).
*The Merck Index*, 10th ed., p. 6063.
*J. Med. Chem.*, vol. 34, p. 616 (1991).

Primary Examiner—David B. Springer
Attorney, Agent, or Firm—Nikaido, Marmelstein, Murray & Oram

[57] ABSTRACT

There are disclosed a benzo[b]furancarboxamide derivative of the formula

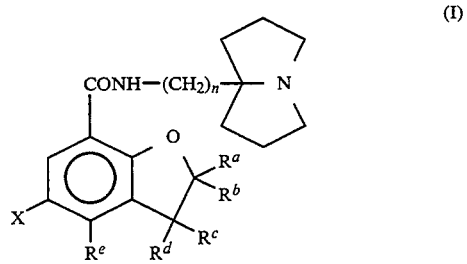

(I)

wherein $R^a$, $R^b$, $R^c$ and $R^d$ are a hydrogen atom or lower alkyl group, respectively; $R^e$ is a hydrogen atom, amino radical, lower alkylamino group or acylamino group; X is a hydrogen atom or halogen atom; and n is an integer of 1–5, and including racemic compounds and stereo-isomers thereof, a salt of the compounds, a process for the preparation of the compounds and salts as well as use thereof for improving hypermotility.

6 Claims, No Drawings

BENZO[B]FURANCARBOXAMIDE DERIVATIVES, PROCESS FOR THE PREPARATION OF SAME AND USE THEREOF FOR IMPROVING HYPERMOTILITY

BACKGROUND OF THE INVENTION

1. Field of the Invention

The present invention relates to novel benzo[b]furancarboxamide derivatives, stereo-isomers thereof, process for the preparation of same, and medicine for improving hypermotility of digestive tract, which contains the compound or salt as an effective ingredient.

2. Related Arts

Since 4-amino-5-chloro-N-[(2-diethylamino)ethyl]-2-methoxybenzamide [General name: Metocloplamide ("The Merck Index", 10th Ed. 6063)] had been developed in the 1960s, as an agent for improving hypermotility of digestive tract or anti-vomiting agent, various benzamide derivatives have been synthesized to evaluate pharmacological effect thereof. The main object for developing such derivatives lies in moderating a side effect of Metoclopramide to central system due to its anti-dopamine action, namely extrapyramidal disorder and cryptorrhea (lactation and prolactinemia), and recent years, various reports have been issued on development of derivatives having antagonism to serotonin receptor. A relation between a selective action and structure of these benzamide derivatives has not sufficiently been elucidated, but it has been recognized that a mutual relation between a substituent to amide nitrogen and alkoxy group at 2-position is important [for instance, Jap. Pat. No. Sho 62 (A.D. 1987)—129279 (A) and "J. Med. Chem.", Vol. 34, page 616 (1991)]. Under such a technical notion, carboxamide derivatives of benzofuran and benzopyran have been studied, as compounds analogous to the benzamide derivatives [Jap. Pat. Nos. Sho 60 (A.D. 1985—169473(A), Sho 62 (A.D. 1987)—234083(A), Hei 1 (A.D. 1989)—104272(A), Hei 1 (A.D. 1989)—110684(A), Hei 1 (A.D. 1989)—168686, Hei 1 (A.D. 1989)—501226(A) and Hei 4 (A.D. 1992)—295476(A)].

SUMMARY OF THE INVENTION

An object of the present invention is to provide a novel compound which has excellent or powerful action to improve hypermotility of digestive tract and no or weak side effect to central system, and thus is excellent in effectiveness and safety.

The inventors have energetically studied and investigated to finally found that certain benzo[b]furancarboxamide derivatives are suitable for attaining the object, so that the invention was established.

The benzo[b]furancarboxamide derivatives are shown by a formula of

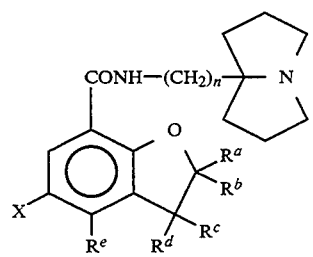

(I)

wherein $R^1$, $R^b$, $R^c$ and $R^d$ are a hydrogen atom or lower alkyl group, respectively; $R^e$ is a hydrogen atom, amino radical, lower alkylamino group or acylamino group; X is a hydrogen atom or halogen atom; and n is an integer of 1–5.

According to a process of the invention, the derivatives (I) and salts thereof can be prepared by reacting a compound of the formula

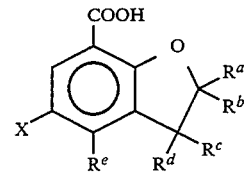

(II)

wherein $R^a$, $R^b$, $R^c$, $R^d$ and $R^e$ have the meanings as referred to, or a reactive derivative thereof with a compound of the formula

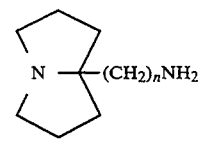

(III)

wherein n has the meaning as referred to, and if necessary, converting a reaction product into the salt.

In connection with the compounds (I), the lower alkyl group is such a straight- or branched-chain alkyl group as methyl, ethyl propyl, isopropyl, butyl, heptyl and hexyl. As examples of the acylamino group, acetylamino and propionylamino radicals may be listed. The halogen atom may be of fluorine, chlorine, bromine or iodine.

The salt of the compounds (I) means, of course, pharmacologically acceptable one, and hydrochloric acid, sulfuric acid, hydrobromic acid or the like inorganic acid; and fumaric acid, oxalic acid, maleic acid, malic acid, tartaric acid, methanesulfonic acid or the like organic acid can be listed as that for forming the salt.

As the reactive derivative of compound (I), a lower alkyl ester, active ester, acid anhydride, acid halide (especially acid chloride) or the like may be listed. As the active ester, p-nitrophenyl ester, 2,4,5-trichlorophenyl ester, pentachlorophenyl ester, cyanomethyl ester, N-hydroxysuccinic imide ester, N-hydroxy-5-norbornen-2.3-dicarboxyimide ester, N-hydroxypiperidine ester, 8-hydroxyquinoline ester, 2-hydroxyphenyl ester, 2-hydroxy-4,5-dichlorophenyl ester, 2-hydroxypyridine ester and 2-pyridylthiol ester can be exemplary listed. As the acid anhydride, a symmetrical acid anhydride or mixed acid arthydride can be employed. As the mixed acid anhydride, any mixture of ethyl chlorocarbonate, isobutyl chlorocarbonate, benzyl chlorocarbonate and the like chlorocarbonic acid esters, or a mixture of the ester with an alkane acid such as isovaleic acid, pivalic acid or the like.

For the reaction between the compounds (II) and (III), a dehydration condensing agent may be added. Such an agent may be listed therefor as dicyclohexylcarbodiimide, hydrochloride of 1-ethyl-3-(3-dimethylaminopropyl)carbodiimide, N,N'-carbonyldiimidazole, 1-ethoxycarbonyl-2-ethoxy-1,2-dihydroquinoline or the like organic condensing agent; and phosphorous trichloride, phosphorous pentachloride, phosphorous oxychloride, thionyl chloride, silicon tetrachloride or the like inorganic condensing agent.

The reaction of the compound (II) or its reactive derivative with the compound (III) can be carried out by stirring for 0.5–24 hours at $-30°-+150°$ C. in an inert solvent. Such a solvent may be exemplary listed as benzene, toluene, xylene or the like aromatic hydrocarbon; diethylether, tetrahydrofuran, dioxane or the like ether; methylene chloride, chloroform or the like halogenated hydrocarbon; pyridine, quinoline, ethyl acetate, acetonitrile, dimethylformamide, dimethylsulfoxide, acetone, ethylene glycol, water, or a mixture of the above. If necessary, the reaction may be carried out in the presence of a base such as sodium carbonate, potassium carbonate or the like alkali carbonate; sodium hydrogen carbonate or the like alkali hydrogen carbonate; sodium hydroxide, potassium hydroxide or the like alkali hydroxide; triethylamine, N-methylmorpholine, N,N-dimethylaniline, pyridine, quinoline or the like tertiary amine. In lieu of separate addition of the base, the compound (III) may be used in excess amount.

The compound shown by Formula (I) and having optical activity can be prepared according to the process as referred to above, but starting from the compound shown by Formula (II) and having optical activity, or by subjecting the racemic compound (II) to optical resolution, in accordance with a conventional method. As the method for carrying out the optical resolution, there are one preparing a salt with an optically active acid (for instance, tartaric acid, dibenzoyl tartaric acid, mandelic acid, camphor-10-sulfonic acid or the like), by utilizing a fact that the racemic compound (I) shows an alkalicity and then subjecting the resulting diastereomers to resolution, a method using a column which separates optical isomers, and the like.

The starting compounds (II) and (III) can be synthesized by methods described, for instance, in Jap. Pat. Nos. Sho 62 (A.D. 1987)—234083(A), Sho 62 (A.D. 1987)—277376(A) and Hei 1 (A.D. 1989)—110684 as well as that described by Miyano et al [" 98 (which can be translated as —Abstract of the 98th Annual Lecture Meeting in the Pharmacological Society of Japan—)", page 223 (1978)], respectively. The compound shown by Formula (II) and having optical activity can be obtained by subjecting the racemic compound (II) to optical resolution in accordance with a method known per se. As the method for carrying out the optical resolution, there are one preparing a salt with an optical active base (for instance, cinchonine, cinchonidine, brucine, quinine, α-methylbenzylamine or the like), by utilizing a fact that the racemic compound (II) shows an acidity and then subjecting the resulting diastereomers to resolution, a method using a column which separates optical isomers, and the like.

When a medicine shall be prepared by using the compound (I) or salt thereof as an effective ingredient, there is no limitation in form of the medicine and thus it can be made into a tablet, pill, capsule, powder, granule, suppository or the like solid preparation; or a solution, suspension, emulsion or the like liquid preparation. For preparing the solid preparation, a starch, lactose, glucose, calcium phosphate, magnesium stearate, carboxymethyl cellulose or the like filler can be used and if necessary, a lubricant, disintegrator, coating agent, coloring matter may also be used. The liquid preparation may contain a stabilizer, dissolution aid, suspending agent, emulsifier, buffer, preservative or the like.

An amount of dose of the compound (I) or salt thereof varies depending on a selected kind of the same, form of the medicine, symptom, age of a patient and other factors, but in general, such a range of about 0.01—about 50 mg/day is preferable for an adult.

DETAILED DESCRIPTION OF PREFERRED EMBODIMENTS

The invention will now be further explained in more detail with reference to Manufacturing Examples, Pharmacological Test Examples and Medicine Preparation Examples.

EXAMPLE 1

4-Amino-N-[2-(1-azabicyclo[3.3.0]octan-5-yl)ethyl]-5-chloro-2,3-dihydrobenzo[b]furan-7-carboxamide Into an agitating solution of 4-amino-5-chloro-2,3-dihydrobenzo[b]furan-7-carboxylic acid (3.21 g) in absolute tetrahydrofuran (50 ml), was added little by little 1,1-carbonylimidazole (2.43 g) and after lapsed 1 hour, a solution of 5-(2-aminoethyl)-1-azabicyclo[3.3.0]octane (2.31 g) in absolute tetrahydrofuran (2 ml) was added therein to reflux for 1 hour. After cooled, the solvent was distilled out in vacuo, a residue was dissolved into chloroform, washed with saturated sodium hydrogen carbonate solution and then water, and thereafter, the solvent was distilled out in vacuo. The resulting residue was refined by alumina column chromatography (developing solvent: chloroform) to afford 4.1 g of the titled compound.

Melting point: 124.5° C.
Mass spectrum (EI/DI) m/z: 349 (M+), 110.
IR spectrum; ν (KBr, max) cm$^{-1}$: 3395, 1625.
NMR spectrum (CDCl$_3$) δ ppm: 1.50–1.85 (10H, m), 2.50–2.65 (2H, m), 2.93–3.08 (2H, m), 3.05 (2H, m), 3.42–3.54 (2H, m), 4.21 (2H, broad), 7.87 (1H, s), 8.28 (1H, broad).

EXAMPLE 2

4-Amino-N-[2-(1-azabicyclo[3.3.0]octan-5-yl)ethyl]-5-chloro-2-methyl-2,3-dihydrobenzo[b]furan-7-carboxamide By treating as described in Example 1 excepting that 4-amino-5-chloro-2-methyl-2,3- dihydrobenzo[b]furan-7-carboxylic acid (5.0 g) was selected as a starting compound, the titled compound (6.68 g) was obtained.

Melting point: 127°–129° C.
Mass spectrum (EI/DI) m/z: 3 (M+), 110.
IR spectrum; ν (KBr, max) cm$^{-1}$: 3395, 1620.
NMR spectrum (CDCl$_3$) δ ppm: 1.52 (3H, d), 1.52–1.83 (10H, m), 2.55–2.68 (3H, m), 2.97–3.06 (2H, m), 3.16 (1H, double d), 3.45–3.53 (2H, m), 4.18 (2H, broad), 5.07–5.15 (1H, m), 7.99 (1H, s), 8.79 (1H, broad).

The resulting free base was treated with fumaric acid in ethanol to obtain corresponding ½ fumarate in quantitative amount.

Melting point: ~200° C. (dec.).

REFERENCE EXAMPLE (+)- and
(−)-4-Amino-5-chloro-2-methyl-2,3-dihydrobenzo[b]furan-7-carboxylic acid 4-Amino-2-methyl-2,3-dihydrobenzo[b]furan-7-carboxylic acid (5.0 g) and anhydrous brucine (8.3 g) were added into methanol (200 ml) to heat the same for dissolving the compounds. Then, formed crystals were obtained by filtration and recrystallization from methanol was repeated to afford brucine salt of 4-amino-2-methyl-2,3-dihydrobenzo[b]furan-7-carboxylic acid. The salt was treated by sodium hydroxide and hydrochloric acid to obtain (+)-4-amino-2-methyl-2,3-dihydrobenzo[b]furan-7-carboxylic acid (200 mg) which was dissolved into N,N-dimethylformamide (1.5 ml) and N-chlorosuccinic imide (119 mg) was added to stir the mixture for 1 hour at 70°–80° C. The reaction solution was poured into an ice and water to obtain by filtration formed crystals which are (+)-4-amino-5-chloro-2-methyl-2,3-dihydrobenzo[b]furan-7-carboxylic acid and can be obtained in quantitative amount.

While, the aforesaid methanol solution (filtrate) was concentrated and refined, and then treatments similar to the above were carried out to obtain (−)-4-amino-5-chloro-2-methyl-2,3-dihydrobenzo[b]furan-7-carboxylic acid.

EXAMPLE 3

(−)-4-Amino-N-[2-(1-azabicyclo[3.3.0]octan-5-yl)ethyl]-5-chloro-2-methyl-2,3-dihydrobenzo[b]furan-7-carboxamide . ½ fumarate By treating as described in Example 1 excepting that (+)-4-amino-5-chloro-2-methyl-2,3-dihydrobenzo[b]furan-7-carboxylic acid (200 mg) obtained by the Reference Example was selected as a starting compound, (+)-4-amino-N-[2-(1-azabicyclo[3.3.0]octan-5yl)ethyl]-5-chloro-2-methyl-2,3-dihydrobenzo[b]furan-7-carboxamide (240 mg) was obtained.

The free base was treated with fumaric acid in ethanol to obtain the titled salt in quantitative amount.

Melting point: ~200° C. (dec.).
$[\alpha]_D$: −3.20° (c=5, methanol:water=1:1).

EXAMPLE 4

(+)-4-Amino-N-[2-(1-azabicyclo[3.3.0]octan-5-yl)ethyl]-5-chloro-2-methyl-2,3-dihydrobenzo[b]furan-7-carboxamide . ½ fumarate By treating as described in Example 1 excepting that (−)-4-amino-5-chloro-2-methyl-2,3-dihydrobenzo[b]furan-7-carboxylic acid (300 mg) obtained by the Reference Example was selected as a starting compound, (−)-4-amino-N-[2-(1-azabicyclo[3.3.0]octan-5-yl)ethyl]-5-chloro-2-methyl-2,3-dihydrobenzo[b]furan-7-carboxamide (350 mg) was obtained.

The free base was treated with fumaric acid in ethanol to obtain the titled salt in quantitative amount.

Melting point: ~200° C. (dec.).
$[\alpha]_D$: +3.46° (c=5, methanol:water=1:1).

EXAMPLE 5

4-Amino-N-[2-(1-azabicyclo[3.3.0]octan-5-yl)ethyl]-5-chloro -2,2-dimethyl-2,3-dihydrobenzo[b]furan-7-carboxamide By treating as described in Example 1 excepting that 4-amino-5-chloro-2,2-dimethyl-2,3-dihydrobenzo[b]furan-7-carboxylic acid (4.08 g) was selected as a starting compound, the titled compound (5.63 g) was obtained.

Melting point: 189°–191° C.
Mass spectrum (EI/DI) m/z: 377 (M+), 110.
IR spectrum; ν (KBr, max) cm$^{-1}$: 3327, 1622.
NMR spectrum (CDCl$_3$) δ ppm: 1.54 (6H, s), 1.55–1.89 (10H, m), 2.56–2.64 (2H, m), 2.84 (2H, s), 2.98–3.07 (2H, m), 3.45–3.53 (2H, m), 4.17 (2H, broad), 7.76 (1H, broad), 7.88 (1H, s).

EXAMPLE 6

4-Amino-N-[2-(1-azabicyclo[3.3.0]octan-5-yl)ethyl]-5-chloro-2,3-dimethyl-2,3-dihydrobenzo[b]furan-7-carboxamide and its ½ fumarate By treating as described in Example 1 excepting that 4- amino-5-chloro-2,3-dimethyl-2,3-dihydrobenzo[b]furan-7-carboxylic acid (100 mg) was selected as a starting compound, 4-amino-N-[2-(1-azabicyclo[3.3.0]octan-5-yl)ethyl]-5-chloro-2,3-dimethyl-2,3dihydrobenzo [b]furan-7-carboxamide (134 mg) was obtained. The free base was treated with fumaric acid in ethanol to obtain its ½ fumarate in quantitative amount.

Melting point: 227°–234° C.
Mass spectrum (EI/DI) m/z: 377 (M+), 110.
NMR spectrum (DMSO-d$_6$) δ ppm: 0.96 (3H, t), 1.57–1.90 (12H, m), 2.63–2.77 (3H, m), 3.00–3.70 (5H, m), 4.87–4.99 (1H, m), 5.70 (2H, broad s), 6.46 (1H, s), 7.47 (1H, s), 7.82 (1H, broad t).

EXAMPLE 7

4-Amino-N-[2-(1-azabicyclo[3.3.0]octan-5-yl)ethyl]-5-chloro-2-ethyl-2,3-dihydrobenzo[b]furan-7-carboxamide and its ½ fumarate By treating as described in Example 1 excepting that 4- amino-5-chloro-2-ethyl-2,3-dihydrobenzo[b]furan-7-carboxylic acid (100 mg) was selected as a starting compound, 4-amino-N-[2-(1azabicyclo [3.3.0]octan-5-yl)ethyl]-5-chloro-2-ethyl-2,3dihydrobenzo [b]furan-7-carboxamide (84 mg) was obtained. The free base was treated with fumaric acid in ethanol to obtain its ½ fumarate in quantitative amount.

Melting point: 174°–176° C.
Mass spectrum (EI/DI) m/z: 377 (M+), 110.
NMR spectrum (DMSO-d$_6$) δ ppm: 0.98, 1.19, 1.31, and 1.45 (6H, each d), 1.62–1.91 (10H, m), 2.69–2.77 (2H, m), 3.00–3.70 (5H, m), 4.61, and 4.87 (1H, each m), 5.68, and 5.75 (1H, each broad d), 6.45 (1H, s), 7.48, and 7.50 (1H, each s), 7.87, and 7.98 (1H, each broad t).

EXAMPLE 8

4-Acetylamino-N-[2-(1-azabicyclo[3.3.0]octan-5-yl)ethyl]-5-chloro-2-methyl-2,3-dihydrobenzo[b]furan-7-carboxamide By treating as described in Example 1 excepting that 4-acetylamino-5-chloro-2-methyl-2,3-dihydrobenzo[b]furan-7-carboxylic acid (100 mg) was selected as a starting compound, the titled compound (145 mg) was obtained.

Mass spectrum (EI/DI) m/z: 405 (M+), 110.
NMR spectrum (CDCl$_3$) δ ppm: 1.52 (3H, d), 1.52–1.83 (10H, m), 2.23 (3H, s), 2.58–2.64 (3H, m), 2.87 (1H, double d), 3.00–3.04 (2H, m), 3.34 (1H, double d), 3.52 (2H, q), 5.05–5.13 (1H, m), 7.26 (1H, broad), 7.98 (1H, s), 8.39 (1H, broad).

EXAMPLE 9

N-[2-(1-Azabicyclo[3.3.0]octan-5-yl)ethyl]-5-chloro -2-methyl -2,3-dihydrobenzo[b]furan-7-carboxamide By treating as described in Example 1 excepting that 5-chloro-2-methyl-2,3-dihydrobenzo[b]furan-7-carboxylic acid (100 mg) was selected as a starting compound, the titled compound (155 mg) was obtained.

Mass spectrum (EI/DI) m/z: 349 (M+), 110.
NMR spectrum (CDCl$_3$) δ ppm: 1.57 (3n, d), 1.52–1.83 (10n, m), 2.56–2.62 (2H, m), 2.87 (1H, double d), 2.98–3.04 (2H, m), 3.36 (1H, double d), 3.48–3.56 (2H, q), 5.03–5.09 (1H, m), 7.20, and 7.89 (1H, each d), 7.98 (1H, s), 8.35 (1H, broad t).

EXAMPLE 10

4-Amino-N-[2-(1-azabicyclo[3.3.0]octan-5-yl)ethyl]-2-methyl -2,3-dihydrobenzo[b]furan-7-carboxamide A mixture of 4-amino-N-[2-(1-azabicyclo[3.3.0]octan-5yl)ethyl]-5-chloro-2-methyl-2,3-dihydrobenzo[b]furan-7-carboxamide (100 mg) obtained by Example 2, 20% Pd-C (catalystic amount) and ethanol was stirred under hydrogen gas atmosphere for 20 hours. Then, the catalyst was removed by filtration and the solvent was distilled out in vacuo to afford the titled compound in quantitative amount.

Mass spectrum (EI/DI) m/z: 329 (M+), 110.

NMR spectrum (CDCl$_3$) δ ppm: 1.52 (3H, d), 1.52–1.87 (10H, m), 2.55–2.66 (3H, m), 2.98–3.06 (2H, m), 3.13 (1H, double d), 3.46–3.53 (2H, m), 3.82 (1H, broad s), 5.02–5.10 (1H, m), 6.27, and 7.77 (1H, each d), 7.92 (1H, broad t).

PHARMACOLOGICAL TEST EXAMPLE 1

Action on Hypermotility of Digestive Tract

The compounds obtained by Examples 1, 2 and 5 as well as exemplar known compounds (Metocloplamide and Cysapride) were selected as Test Compounds, and an action of the compounds for accelerating gastric emptying was checked in accordance with the method described by Yokochi et al [" (which can be translated as —Bulletin of Pharmacological Society of Japan—)", Vol. 92, page 297 (1988 )].

Namely, the test compound was orally administered in an amount of 0.3, 1.0, 3.0 or 10 mg/kg to rats fasted for 24 hours, and after 30 minutes from the administration, a coloring matter in a constant amount (phenol red, 100 μg) was also orally administered. After 15 minutes from the administration of coloring matter, gastric pylorus and cardia were ligated to exentrate a stomach and to measure an amount of the coloring matter remaining in the stomach through a measurement of absorbance at 560 nm for calculating a rate of gastric emptying and rate of its acceleration., in accordance with following equations, so that an effective amount (ED$_{50}$) was determined.

Rate of gastric emptying = 100 − (B/A) × 100
A: Dosing amount of coloring matter, and
B: Remaining amount of coloring matter.
Rate of acceleration = (C − D) × 100
C: Rate of gastric emptying in Test Group, and
D: Rate of gastric emptying in Control Group given no Test Compound.

Results are shown in following Table 1. As apparently seen therefrom, each of the compounds according to the invention shows an action for accelerating gastric emptying far excellent from that of the known compounds.

TABLE 1

| Test Compound | ED$_{50}$ (mg/kg) |
|---|---|
| Example | |
| 1 | 2.15 |
| 2 | 1.97 |
| 5 | 1.50 |
| Metoclopramide | 16.3 |
| Cisapride | 6.37 |

PHARMACOLOGICAL TEST EXAMPLE 2

Agonisting Action to 5-HT$_4$ Receptor

Each of the compounds obtained by Examples and Cysapride (exemplar known compound which has been said as having a strong agonisting action to 5-HT$_4$ receptor) were selected as Test Compounds and Control compound, and agonisting action thereof was checked in accordance with the method described by Baxter et al "Naunyn-Schmiederberg's Arch. Pharmacol.", Vol. 343, page 439 (1991)].

Namely, a relaxation of the Test and Control compounds in various concentration showing to carbachol contradiction of a muscular sample of mucous membrane in esophgus exentrated from a rat was checked to calculate a concentration causing 50% relaxation and compared with its negative logarithm (pEC$_{50}$). Results are shown in following Table 2. Therefrom, it has been found that the compounds according to the invention show the agonisting action to 5-HT$_4$ receptor, which is compatible to or excellent than the Control Compound.

TABLE 2

| Compound | pEC$_{50}$ |
|---|---|
| Example | |
| 1 | 6.5 |
| 2 (*) | 7.4 |
| 3 | 7.7 |
| 4 | 7.3 |
| 5 | 6.5 |
| 6 | 7.9 |
| 7 | 7.7 |
| 8 | 6.5 |
| 9 | 7.0 |
| 10 | 6.0 |
| Cisapride | 7.4 |

In the Table, *: ½ fumarate.

PHARMACOLOGICAL TEST EXAMPLE 3

Anti-Dopamine Action

The compounds obtained by Examples 1, 2 and 5 as well as known compounds (Metocloplamide and Cysapride) were selected as Test and Control Compounds, respectively. The compound was orally administered to rats in amount of 100, 300 or 1000 mg/kg to observe for 2 days general symptoms including catalepsy and blepharoptosis due to antagonistic action of the compound to dopamine D$_2$ receptor. Results are shown in following Table 3. As apparently seen therefrom, no anti-dopamine action was recognized on the compounds according to the invention.

TABLE 3

| | Influence on central nervous system ($^a$) | | |
|---|---|---|---|
| Compound | 100 mg/kg | 300 mg/kg | 1000 mg/kg |
| Test | | | |
| Example 1 | | | − |
| 2 | − | − | − |
| 5 | | | |
| Control | | | |
| Metoclopramide | ++ | | |
| Cisapride | | | ++ |

In connection with ($^a$),
−: No influence,
+: Noticeable influence, and
++: Somewhat remarkable influence.

MEDICINE PREPARATION EXAMPLE 1 (TABLET)

Tablets were prepared in conventional manner and by using following ingredients.

| Compound (Example 1) | 2.0 (mg) |
|---|---|
| Lactose | 136.0 |
| Corn starch | 60.0 |
| Magnesium stearate | 2.0 |
| | 200.0 mg/tablet |

MEDICINE PREPARATION EXAMPLE 2 (INJECTION)

An injection was prepared in conventional manner and by using following ingredients. The injection was charged into ampules under aseptic condition to heat seal the ampules. When it shall be used, the solution in the ampule may be diluted with a saline for injection.

| Compound (Example 2, ¼ fumarate) | 0.05 (mg) |
|---|---|
| Sodium chloride | 8.00 |
| Distilled water for injection | Remainder |
| | 1.0 ml/ampule |

What is claimed is:

1. A benzo[b]furancarboxamide derivative of the formula

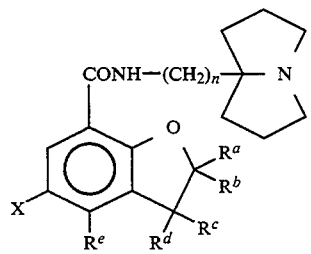

(I)

wherein $R^a$, $R^b$, $R^c$ and $R^d$ are a hydrogen atom or lower alkyl group, respectively; $r^e$ is a hydrogen atom, amino radical, lower alkylamino group or lower alkanoylamino group; X is a hydrogen atom or halogen atom; and n is an integer of 1–5 or a pharmacologically acceptable salt of the compounds.

2. A benzo[b]furancarboxamide derivative as claimed in claim 1, wherein it is selected from the group consisting of (a) 4-amino-N-[2-(1-azabicyclo[3.3.0]octan-5-yl)ethyl]-5-chloro-2,3-dihydrobenzo[b]furan-7-caroxamide, (b) 4-amino-N-[2-(1-azabicyclo[3.3.0]octan-5-yl)ethyl]-5-chloro-2-methyl-2,3-dihydrobenzo[b]furan-7-carboxamide, (c) (+)-4-amino-N-[2-(1-azabicyclo[3.3.0]octan-5-yl)ethyl]-5-chloro-2-methyl-2,3-dihydrobenzo[b]furan-7-carboxamide, (d) (−)-4-amino-N-[2-(1-azabicyclo [3.3. 0]octan-5-yl) ethyl]-5-chloro-2-methyl-2,3-dihydrobenzo[b]furan-7-carboxamide, (e) 4-amino-N-[2-(1-azabicyclo[3.3.9]octan-5-yl)ethyl]-5-chloro-2,2-dimethyl-2,3-dihydrobenzo[b]furan-7-carboxamide, (f) 4-amino-N-[2-(1-azabicyclo[3.3.0]octan-5-yl)ethyl]-5-chloro-2,3-dimethyl-2,3-dihydrobenzo[b]furan-7-carboxamide, (g) 4-amino-N-[2-(1-azabicyclo[3.3.0]octan-5-yl)ethyl]-5-chloro-2-ethyl-2,3-dihydrobenzo[b]furan-7-carboxamide, (h) 4-acetylamino-N-[2-(1-azabicyclo[3.3.0]octan-5-yl)ethyl]-5-chloro-2-methyl-2,3-dihydrobenzo[b]furan-7-carboxamide, (i) N-[2-(1-azabicyclo[3.3.0]octan-5-yl)ethyl-5-chloro-2-methyl-2,3-dihydrobenzo[b]furan-7-carboxamide, and (j) 4-amino-N-[2-(1-azabicyclo[3.3.0]octan-5-yl)ethyl]-2-methyl-2,3-dihydrobenzo[b]fruan-7-carboxamide.

3. A process for the preparation of a benzo[b]furancarboxamide derivative of the formula

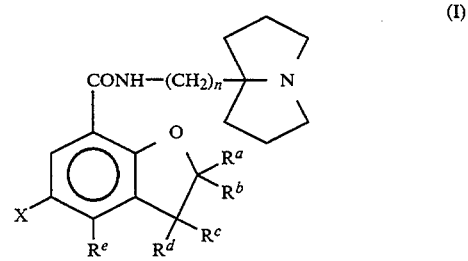

(I)

wherein $R^a$, $R^b$, $R^c$ and $R^d$ are a hydrogen atom or lower alkyl group, respectively; $R^e$ is a hydrogen atom, amino radical, lower alkylamino group or lower alkanoylamine group; X is a hydrogen atom or halogen atom; and n is an integer of 1–5, said process comprising:

a) providing a compound of formula II

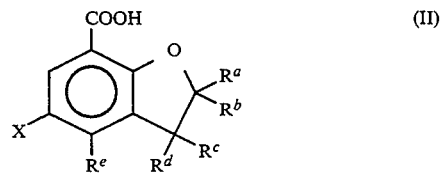

(II)

wherein $R^a$, $R^b$, $R^c$, $R^d$ and $R^e$ have the meanings as referred to, and b) reacting the compound obtained by step (a) with a compound of formula III

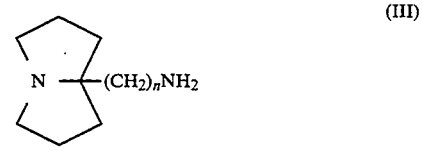

(III)

wherein n has the meaning as referred to, by stirring said compounds for 0.5–24 hours at −30°–+150° C. in an inert solvent.

4. A process for the preparation of a pharmacologically acceptable salt of benzo[b]furancarboxamide derivative of the formula

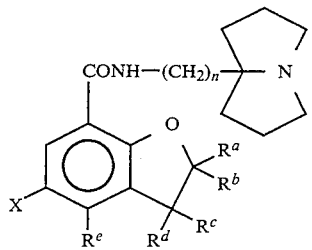

(I)

wherein $R^a$, $R^b$, $R^c$ and $R^d$ are a hydrogen atom or lower alkyl group, respectively; $R^e$ is a hydrogen atom, amino radical, lower alkylamino group or lower alkanoylamino group; X is a hydrogen atom or halogen atom; and n is an integer of 1–5, said process comprising:

a) providing a compound of formula II

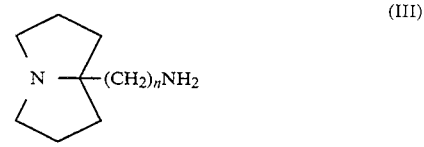

wherein $R^a$, $R^b$, $R^c$, $R^d$ and $R^e$ have the meanings as referred to, and b) reacting the compound obtained by step (a) with a compound of formula III (III)

wherein n has the meaning as referred to, by stirring said compounds for 0.5 0 24 hours at $-30°-+150°$ C. in an inert solvent, and c) converting the resulting compound of Formula I into the salt by a method known per se.

5. A method of improving hypermotility of a digestive tract, said method comprising administering a hypermotility improving effective amount, of the compound or salt of claim 1 to a patient in need of such effect.

6. A method of improving hypermotility of a digestive tract, said method comprising administering a hypermotility improving effective amount, of the compound of claim 2 to a patient in need of such effect.

* * * * *